US00PP09395P

United States Patent [19]

Kirkland et al.

[11] Patent Number: Plant 9,395

[45] Date of Patent: Dec. 5, 1995

[54] ST. AUGUSTINE GRASS 'SS-100'

[75] Inventors: Elmer R. Kirkland, New Smyrna, Fla.; Tobey A. Wagner, Mt. Pleasant, S.C.

[73] Assignee: Sod Solutions, Inc., Mt. Pleasant, S.C.

[21] Appl. No.: 223,854

[22] Filed: Apr. 6, 1994

[51] Int. Cl.[6] ..... A01H 5/00

[52] U.S. Cl. ..... Plt./90.1

[58] Field of Search ..... Plt./90.1

[56] References Cited

U.S. PATENT DOCUMENTS

| | | | |
|---|---|---|---|
| P.P. 2,863 | 2/1969 | Long | Plt./90.1 |
| P.P. 3,180 | 5/1972 | Gruis | Plt./90.1 |
| P.P. 3,491 | 2/1974 | Garrett | Plt./90.1 |
| P.P. 4,097 | 9/1977 | Gruis | Plt./90.1 |
| P.P. 6,126 | 3/1988 | Riordan | Plt./90.1 |
| P.P. 6,372 | 11/1988 | Mixson | Plt./90.1 |
| P.P. 6,921 | 7/1989 | Mixson | Plt./90.1 |
| P.P. 6,922 | 7/1989 | Mixson | Plt./90.1 |
| P.P. 7,699 | 10/1991 | Busey | Plt./90.1 |
| P.P. 7,852 | 4/1992 | Busey | Plt./90.1 |

OTHER PUBLICATIONS

Busey, P., (1986) "Morphological Identification of St. Augustine Cultivars" *Crop Science* vol. 26, Jan.–Feb., pp. 28–32.

Busey, P., et al. (1991) "Turfgrass in Shade Environment" *Proc. Fla. State Hort. Soc.* 104: 353–358.

Augustin, B. J., et al, "St. Augustinegrass for Florida Lawns" (Bulletin) OH5, Florida Department of Ornamental Horticulture.

Callahan et al., DNA fingerprinting of turfgrass. *Golf Course Management,* pp. 80, 82, 86 (Jun. 1993).

*Primary Examiner*—James R. Feyrer

*Attorney, Agent, or Firm*—Bell, Seltzer, Park & Gibson

[57] ABSTRACT

A perennial, vegetatively propagated St. Augustine grass having dark green leaves and having shade tolerance, cold and frost tolerance, and drought tolerance.

7 Drawing Sheets

BACKGROUND OF THE INVENTION

The invention relates to a new and distinct perennial St. Augustine grass discovered on a sod farm near Samsula, Fla., in proximity to plantings of the St. Augustine grasses Bitterblue, Floratam, and an undefined Mississippi grass. The parents of SS-100 are unknown. The grass SS-100 was propagated asexually at Samsula, Fla. and at a test site in Mt. Pleasant, S.C. Asexual propagation was carried out by cutting stolons into segments, each segment containing at least one node, and planting segments directly into the soil and into plug trays. SS-100 is a distinct, asexually propagated variety of St. Augustine grass. The designation SS-100 is short for Sod Solutions-100, which may also designate this plant in commerce. It is also anticipated that the plant of this invention will be marketed under the synonym Palmetto as a tradename. The plant is so identified in portions of the drawings of this disclosure.

SUMMARY OF THE INVENTION

SS-100 is a distinctive dark green St. Augustine grass exhibiting shade tolerance, cold and frost tolerance, and drought tolerance. These traits are maintained when propagated asexually.

BRIEF DESCRIPTION OF THE ILLUSTRATIONS

Figure 5:
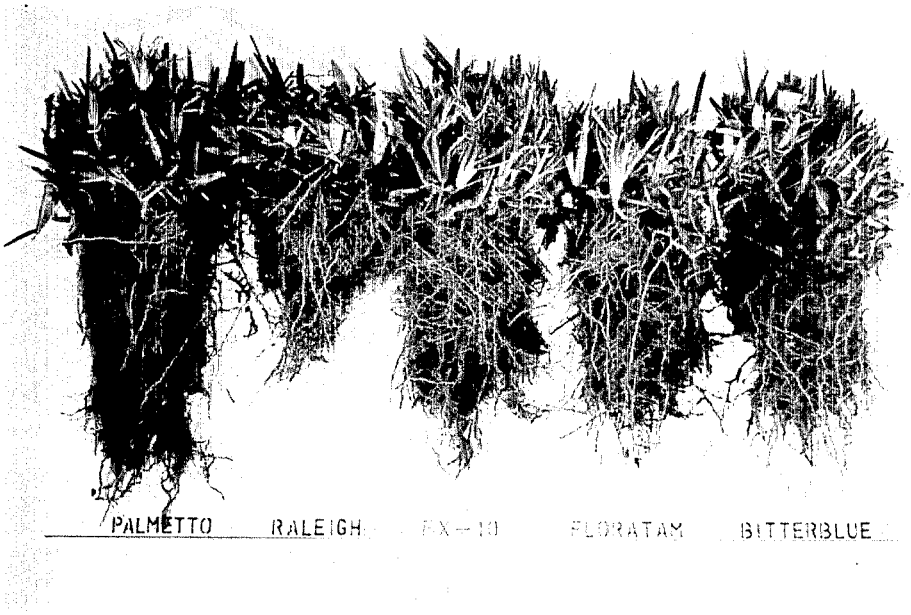

FIG. 5 compares the root systems of SS-100 ("Palmetto"), Raleigh, FX-10, Floratam and Bitterblue field samples.

Figure 6:
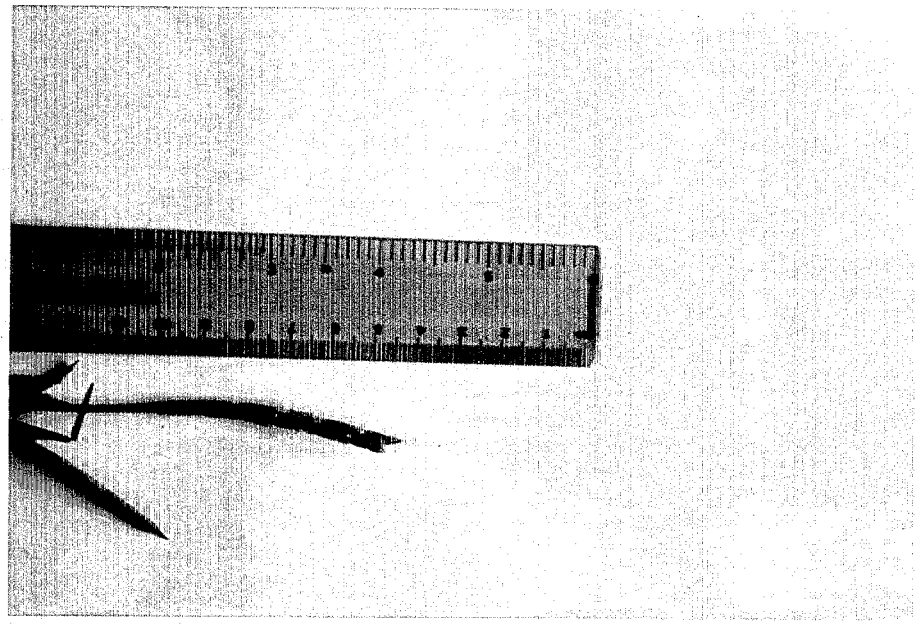

FIG. 6 shows the seed head of SS-100.

Figure 7:
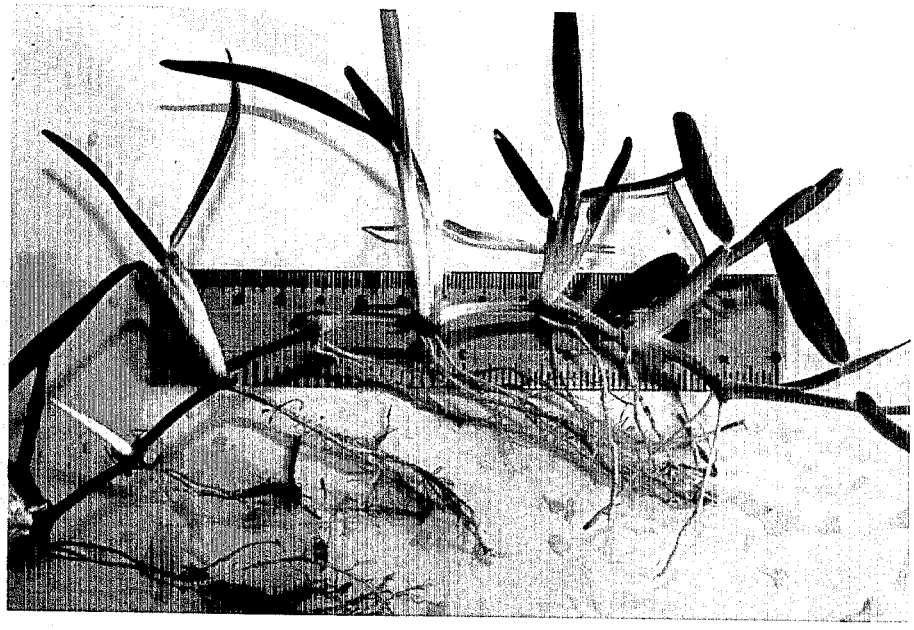

FIG. 7 shows the runner of SS-100.

Figure 8:
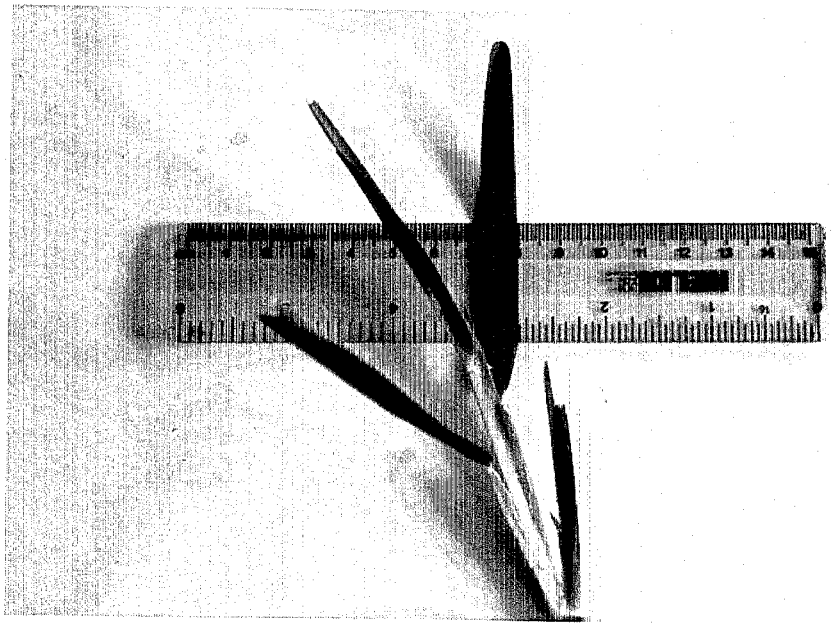

FIG. 8 shows the leaf blade of SS-100.

Figure 9:
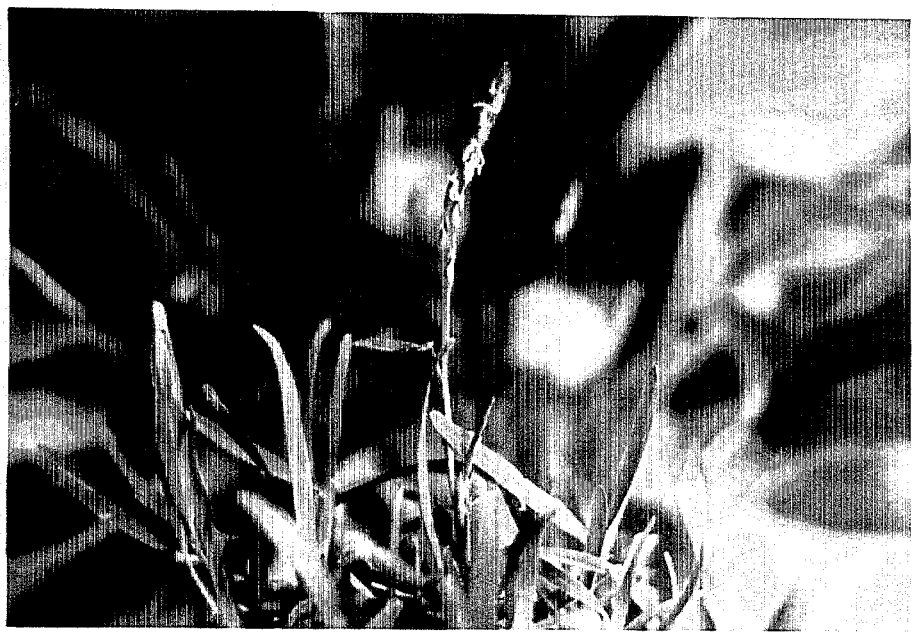

FIG. 9 shows anther and stigma colors of SS-100.

Figure 10:
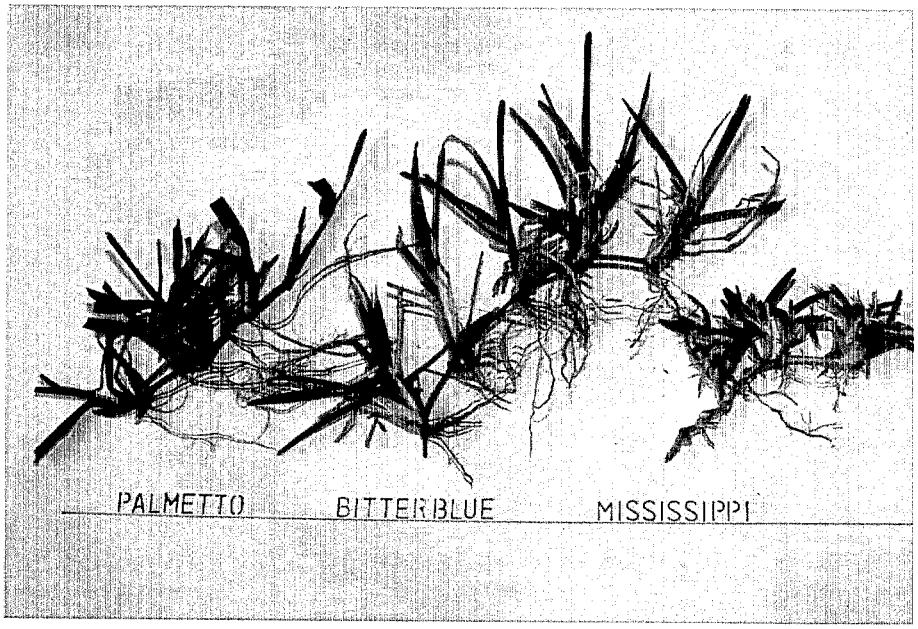

FIG. 10 shows DNA amplification profiles of SS-100 ("Palmetto"), Bitterblue, and the undefined Mississippi grass.

Figure 11:
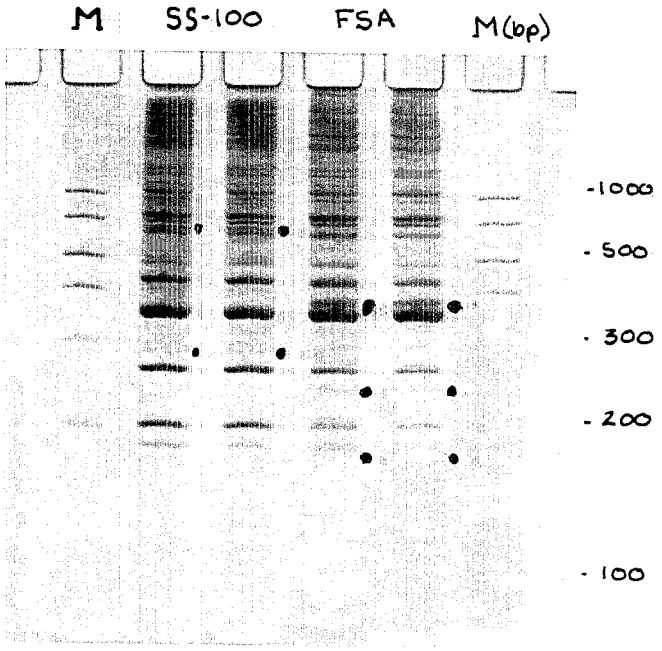

FIG. 11 shows DNA amplification profiles of SS-100 ("Palmetto") and Floratam.

DETAILED DESCRIPTION OF THE VARIETY

The following is a detailed description of the new grass variety, based upon observations of the plant grown in field plots. Color notations are based on the *The Royal Horticultural Society Colour Chart*, The Royal Horticultural Society, London.

SS-100 is a perennial, vegetatively propagated St. Augustine grass (*Stenotaphrum secundatum* [Walt.] Kuntze). It grows by creeping or ascendant stolons which root at the nodes. The flagleaf colr is in green group 137, intermediate greens 137A and 137B (*The Royal Horticultural Society Colour Chart,* The Royal Horticultural Society, London). Applicants have asexually propagated the new grass at locations in Florida and South Carolina by means of stolon cuttings, using segments of stolons containing at least one node. Planting stock was grown from the stolon cuttings for use in studying performance and in comparting to commercially available cultivars. The applicants have discovered the novelty and distinctness of SS-100 compared with other varieties of St. Augustine grass.

1. Color and Dimensions

The overall color of SS-100 is a deep green between Dark Green 262 and Parrot Green 260 (*Naturalist's Color Guide*). When compared to Bitterblue, the undefined Mississippi grass, Floratam, Raleigh and FX-10 (U.S. Plant Pat. No. 7,852), the present variety is most similar in color to Bitterblue, but is a shade darker than Bitterblue when observed in the field. The color of SS-100 is more consistent over a given area without variation in shades of yellow and green as may be observed in Raleigh, Floratam, FX-10, or Bitterblue varieties.

SS-100 has medium to wide leaf blades (FIGS. 7 and 8) similar to Bitterblue, Floratam, and FX-10. The texture of SS-100 is soft to the touch, similar to Bitterblue and unlike Floratam and FX-10 which have a prickly feel. The leaf blades of SS-100 are tapered at the tip with a rounded end as shown in FIG. 8, similar to the undefined Mississippi grass (see FIG. 10). Seedheads of SS-100 are inconspicuous in overall appearance (FIG. 6, FIG. 9) and few in number. Anther color is orange-yellow, stigma color is white, and chromosome number is 18. These characteristics are compared to Bitterblue, Floratam, FX-10 and Raleigh in Table 1 and Table 2.

TABLE 1

Comparative Leaf Blade Width and Internode Length

| Selection/ Variety | Blade Width (mm)[1] | Internode Length (mm)hu 2 |
|---|---|---|
| SS-100 | 9.4 | 19.8 |
| Bitterblue | 9.3 | 36.8 |
| Floratam | 11.0 | 59.6 |
| FX-10 | 10.0 | — |
| Raleigh | 9.2 | 49.2 |
| Mississippi | 7.4 | 20.6 |

[1]Measurement made at widest portion of 10 random samples and averaged.
[2]Measurement made between the third and fourth internode of 5 random samples and averaged.

TABLE 2

| Selection/ Variety | Anther Color[1] | Stigma Color[1] | Chromosome Number[2] |
|---|---|---|---|
| SS-100 | Orange Yellow | White | 18 |
| Bitterblue | Orange Yellow | Purple | 27 |
| Floratam | Orange Yellow | Purple | 27 |
| FX-10 | Orange Yellow | Purple | 30 |
| Raleigh | Sulfur Yellow | White | 18 |

[1]Based on comparison of field samples with the Naturalist'sColorGuide for SS-100.
[2]Chromosome number testing performed at Georgia Coastal Plain Experimental Station, Tifton, Georgia.

2. Growth Characteristics

SS-100 is a deep-rooted St. Augustine grass with fine roots and an extensive root system (see FIG. 5). The root characteristics of SS-100 may explain its drought tolerance, as such plants would have a deeper root system with increased surface area compared to shorter, thicker root. A deeply rooted green stemmed grass such as SS-100 would also be expected to a more cold hardy variety than a purple stemmed shallow rooted variety. To compare root systems, samples of mature SS-100, Raleigh, FX-10, Floratam and Bitterblue grown under similar conditions at a single test site were excavated, taking care to obtain the terminal portions of the roots. When compared, the roots of SS-100 were longer and appeared finer than those of other grasses (FIG. 5).

Spring green-up rates of SS-100 after it has gone dormant have been observed to be two to three weeks faster than Floratam, Bitterblue, the undefined Mississippi grass, FX-10, and Centipede, as observed in Samsula, Fla., test plots grown under similar conditions, and in Mt. Pleasant, S.C., test plots grown under similar conditions.

Minimal shock has been observed in SS-100 after transplantation when adequate water is supplied during the first few weeks of establishment. Root systems 2–4 inches deep in the soil have been observed 7–14 days after the transplant process, with vigorous growth occurring from the top surface material.

SS-100 spreads rapidly horizontally similar to Floratam and Bitterblue in the field and test plots. The vertical growth has been noted to be less than Bitterblue under similar growing conditions.

3. Drought Tolerance

At the Samsula, Fla. site where SS-100 was discovered and asexually reproduced, tolerance to drought was observed. In the summer of 1993 no rainfall occurred for seven weeks. The test site was not irrigated. While detailed observations were not taken at that time, Applicant observed that SS-100 and FX-10 had only a slight reduction in canopy coverage, while Floratam, Bitterblue, Raleigh, Seville (U.S. Plant Pat. No. 4,097), the undefined Mississippi and Delmar (U.S. Plant Pat No. 6,372) grasses demonstrated severe loss of canopy coverage. Once established, SS-100 has an extensive root system similar to FX-10 which could decerease frequency and amount of irrigation needed.

4. Shade Tolerance

SS-100 has been observed to grow in shaded areas where no direct sunlight occurs. In Samsula, Fla., SS-100 successfully grew under mature live oak trees which prevented direct sunlight from reaching the ground. While shade tolerance is difficult to quantitatively define, SS-100 performed well in various heavily shaded test plots in Florida and South Carolina where other shade tolerant St. Augustine grasses such as Bitterblue, Raleigh, and Jade had failed. Although overall turf thickness of SS-100 was reduced in conditions of heavy shade compared to SS-100 grown in full sun, SS-100 maintained a dark green appearance in heavily shaded test plots where previous plantings of Floratam, Raleigh, and Jade had unsatisfactory results, as noted by the Applicant.

In Orange City, Fla., SS-100 has shown good results in a large heavily shaded test area where several varieties of St. Augustine grasses gradually declined. In this area, the SS-100 had a pleasing overall appearance with consistent color among areas exposed to varying amounts of light. No known St. Augustine, including SS-100, can survive in total shade (i.e., absence of light) but SS-100 has survived in heavily shaded areas with no noticeable change in color.

5. Cold Tolerance

Winter temperatures of the Southeastern United States were generally warm, but occasional severe cold snaps occur. St. Augustine varieties such as Floratam, Bitterblue and FX-10 can be permanently damaged or killed by such cold weather. Varieties such as Raleigh have been developed for cold resistance.

At the Columbia, S.C., test site the temperature fell to 10° F. during January of 1994. SS-100 and Raleigh survived with only minimal damage to stolons while Floratam, Bitterblue, and FX-10 experienced heavy damage (Table 3). In a test site near Spartanburg, S.C. during the same time period the temperature fell to 3° F., and did not exceed 32° F. for over seven consecutive days. SS-100 and Raleigh both suffered minor damage from which they would be expected to fully recover (Table 4). Temperatures were recorded by a HI-Q Thermograph (WEATHERtronics, Sacramento, Calif.).

TABLE 3

| Cold Damage to Stolons | |
|---|---|
| Selection/Variety | % Stolon Kill[1] |
| SS-100 | 10% |
| Raleigh | 15% |
| Bitterblue | 95% |
| Floratam | 99% |
| FX-10 | 99% |
| Centipede | 10% |

[1]Based on % of cold damage to stolons as observed 30 days after a minimum temperature of 10° F. in January 1994; all varieties grown at same site under similar conditions.

TABLE 4

| Cold Damage to Stolons | |
|---|---|
| Selection/Variety | % Stolon Kill[1] |
| SS-100 | 20% |
| Raleigh | 25% |

[1]Based on % of cold damage to stolons observed 30 days after a minimum temperature of 3° F. recorded in January 1994; varieties grown at same site under similar conditions.

6. Frost Tolerance

SS-100 has been shown in field studies to be more frost tolerant than Floratam, Raleight, Bitterblue, or FX-10 varieties of St. Augustine grass, and common Centipede. SS-100 has remained green during winters with temperatures below freezing, as observed by Applicant. In a comparison of Raleigh and SS-100 sod laid 2 months previously in field conditions in Spartanburg, S.C., the grasses were compared after the first two nights of heavy frost in Fall 1993, during which the temperature was recorded as 28° F. and 23° F., respectively. Following this period of heavy frost, SS-100 had better color and growth rate and less frost damage than Raleigh (Table 5).

TABLE 5

| | Color[1] | Growth Rate[2] | Frost Damage[3] |
|---|---|---|---|
| Raleigh | 3 | 2 | 70% |
| SS-100 | 8 | 8 | 10% |

[1]Based on 1 to 10 scale which subjectively rated color intensity and uniformity after frost cycles, with 10 being most pleasing and 1 being least.
[2]Based on overall growth rate (horizontal and vertical) during two months in Fall 1993.
[3]Based on visual rating of percentage of canopy that was browned.

A comparison of sod laid two months earlier in Columbia, S.C., was conducted after a night of heavy frost when temperatures fell to 28 degrees fahrenheit. SS-100 was noted to have better color and growth rate than Raleigh, FX-10 and Bitterblue (TABLE 6). SS-100 experienced less frost damage than Centipede, Raleigh, FX-10 and Bitterblue, and was comparable to Floratam (TABLE 7).

TABLE 6

| | Color[1] | Growth Rate[2] | Frost Damage[3] |
|---|---|---|---|
| Centipede | 1 | 2 | 95% |
| Raleigh | 3 | 3 | 70% |
| FX-10 | 5 | 5 | 50% |
| Bitterblue | 7 | 6 | 30% |
| Floratam | 9 | 8 | 10% |
| SS-100 | 8 | 6 | 10% |

[1]Based on 1 to 10 scale which subjectively rated color intensity and uniformity after frost cycles, with 10 being most pleasing and 1 being least.
[2]Based on overall growth rate (horizontal and vertical) during two months in Fall 1993.
[3]Based on visual rating of percentage of canopy that was browned.

Figure 1:
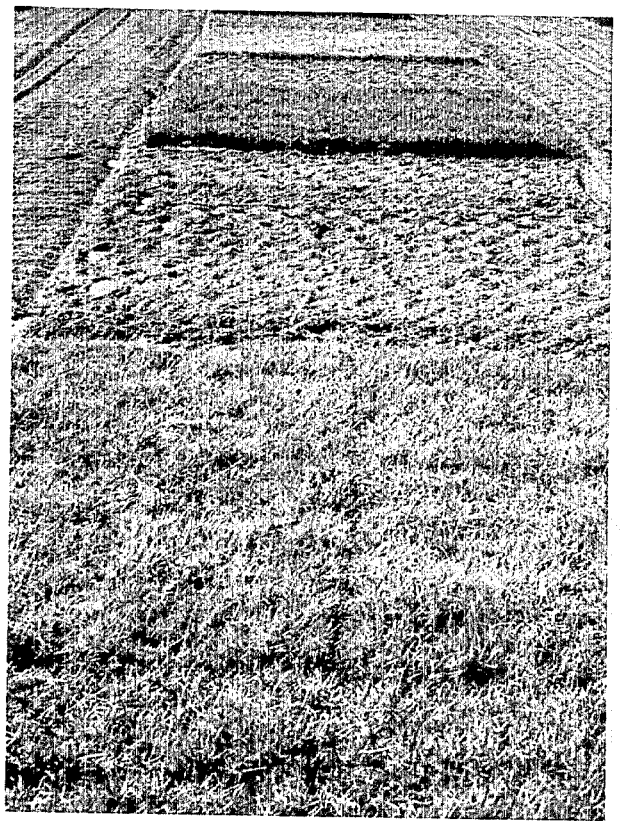
FIG. 1 shows the overall appearance of Bitterblue (foreground, at A) compared to SS-100 (background, at B) following a period of frost.
Figure 2:
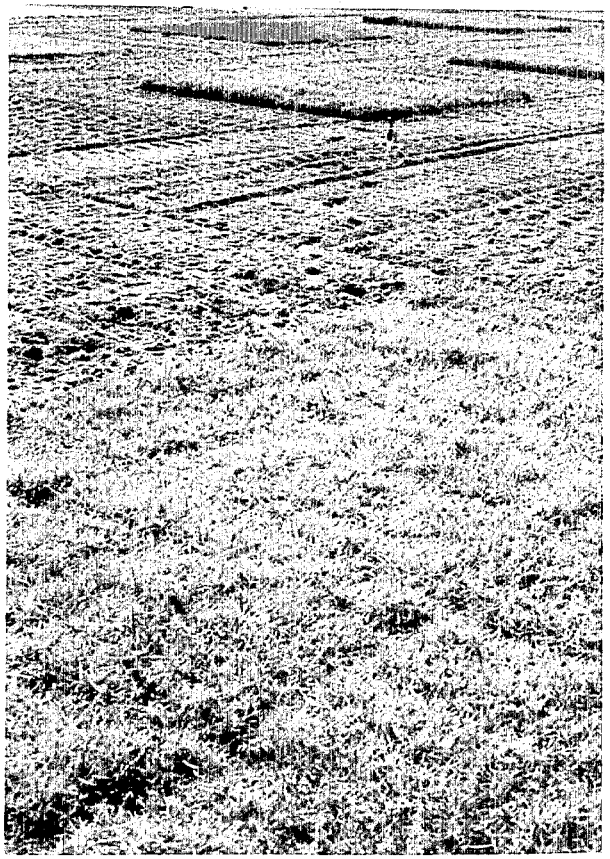
FIG. 2 shows the overall appearance of Raleigh (foreground, at A) compared to SS-100 (background, at B) following a period of frost.
Figure 3:
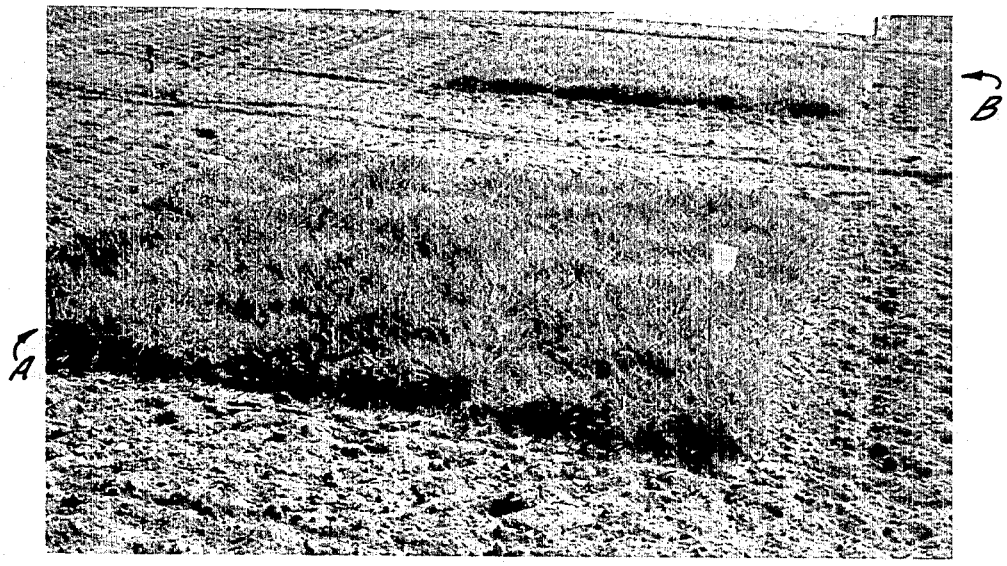
FIG. 3 shows the overall appearance of FX-10 (foreground, at A) compared to SS-100 (background, at B) following a period of frost.
Figure 4:
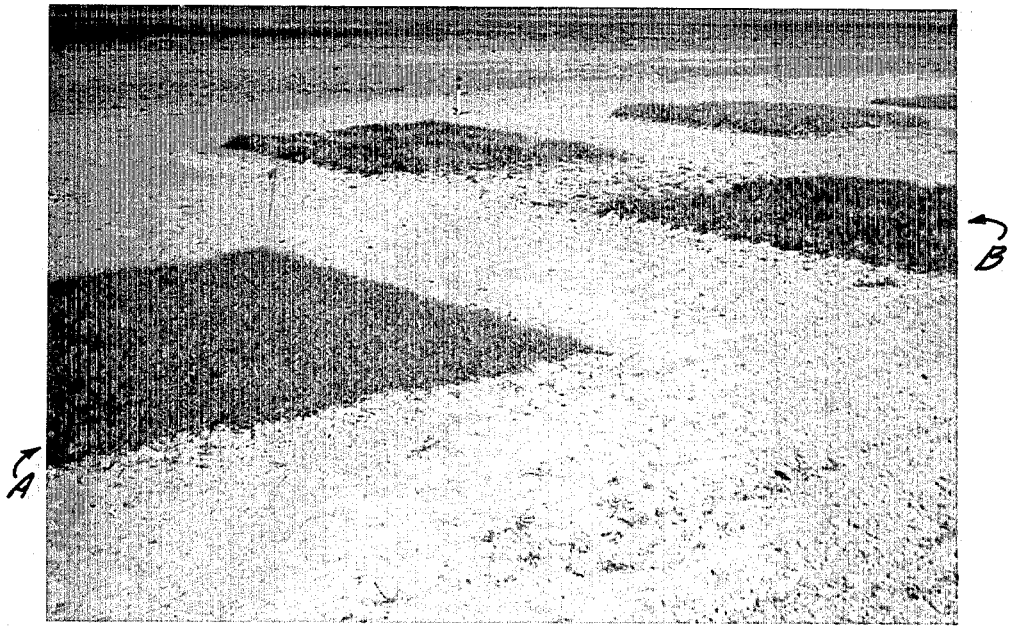
FIG. 4 shows the overall appearance of Centipede (left foreground, at A) compared to SS-100 (right midground, at B) following a period of frost.

A comparison of the color and dormancy of sod test plots at Columbia, S.C., was conducted after three series of frosts (a total of seven non-consecutive mornings of below freezing temperatures) (TABLE 7). SS-100 was noted to have better color and less dormancy than Bitterblue (FIG. 1), Raleigh (FIG. 2), FX-10 (FIG. 3), Centipede (FIG. 4), and Floratam (not shown). The SS-100 test plot was clearly discernable from the other test plots in both color and dormancy rate at this time. This characteristic may allow SS-100 to be evergreen or semi-evergreen (e.g., the bottom layer of stolons maintains green leaves) in areas of the south where frosts rarely occur. Presently, St. Augustine varieties that are less frost tolerant go completely dormant for many weeks or months. A test site of SS-100 located at Edisto Island, S.C., has remained green through the winter in shaded areas where temperature fell to 19° F. during January. No other commercially available variety of St. Augustine has shown this degree of cold and frost tolerance.

TABLE 7

| | Color[1] | Frost Damage[2] |
|---|---|---|
| Centipede | 1 | 100% |
| Raleigh | 1 | 100% |
| FX-10 | 2 | 95% |
| Bitterblue | 2 | 95% |
| Floratam | 2 | 90% |
| SS-100 | 5 | 50% |

[1]Based on 1 to 10 scale which subjectively rated color intensity and uniformity, with 10 being most pleasing and 3 being least.
[2]Based on visual rating of percentage of canopy that was browned.

7. Disease Resistance

Gray leaf spot affects all St. Augustine varieties to varying degrees. Gray leaf spot has been observed on SS-100 in a limited coverage area during extremely humid and wet conditions in Samsula, Fla.; no appreciable effect on the overall color or growth rate of SS-100 was noted. During this same period the undefined Mississippi grass which was in proximity to the site where SS-100 was discovered was extensively damaged by gray leaf spot, such that it was not suitable for use as turf. Neither SAD virus or Brown Patch have been detected in SS-100 test plots to date.

8. DNA Analysis

Comparative DNA amplification profiles of SS-100 and Floratam produced by the University of Tennessee Molecular Genetics Laboratory are shown in FIG. 11, where M is the molecular marker lane, "Palmetto" denotes SS-100 (two lanes), and ESA denotes Floratam St. Augustine grass (two lanes). The profiles were generated using known DNA amplification fingerprinting (DAF) techniques; see e.g., Caetano-Anolles et al., BIO/Technology, 9, 553 (1991); Callahan et al, *Golf Course Management,* Study asset100 and Floratam were determined to be page 80 (June 1993). Based on this genetically distinct.

9. Rate of Growth

On Feb. 3rd, 1994, four separate plots measuring eight feet by eight feet were planted in New Smyrna Beach, Fla., using 4-inch plugs of St. Augustine grass spaced 18 inches on center. One plot each was planted with SS-100, Floratam, Bitterblue, and Raleigh. Each plot was fertilized with a 16-4-8 blend on each of March 14, May 11, and July 12. The plots were planted essentially side-by-side, and soil, irrigation, sunlight and other growing conditions were essentially identical.

Table 7 provides information on growth of the grasses in the test plots. Percentage of coverage was assessed subjectively by a single observer once each month, where the initial planting by plus was defined as providing 5% coverage and 100% coverage was defined as when the ground was first completely covered with grass runners. As shown in Table 7, 100% coverage was provided by SS-100 at seven months of growth, while 100% coverage was not provided by Floratam, Bitterblue and Raleigh until eight, nine and ten months of growth, respectively.

TABLE 7

| Month | SS-100 | FLORATAM | BITTERBLUE | RALEIGH |
|---|---|---|---|---|
| Feb. | 5% | 5% | 5% | 5% |
| March | 20% | 25% | 25% | 15% |
| April | 40% | 45% | 40% | 30% |

TABLE 7-continued

| Month | SS-100 | FLORATAM | BITTERBLUE | RALEIGH |
|---|---|---|---|---|
| May | 55% | 55% | 50% | 45% |
| June | 70% | 65% | 60% | 55% |
| July | 90% | 85% | 75% | 60% |
| August | 100% | 90% | 80% | 70% |
| Sept. | | 100% | 90% | 75% |
| October | | | 100% | 90% |
| Nov. | | | | 100% |

It was noted that as Palmetto put out runners, each stolon established a root system at each individual node, even out to the last node on the stolon. This contrasted with Bitterblue and Floratam, in which the runners did not establish root systems at each node until the runner had extended four to five node lengths.

Sod grown for commercial use it not necessarily ready for harvest when 100% coverage (as defined above) has been reached. Overlapping of stolons must occur before the sod will "block up" to enable harvesting. SS-100, due to its aggressive root system can be harvested at 100% coverage as has been demonstrated by several licensed growers of SS-100. In the case of Floratam, Bitterblue and Raleigh, sod cannot necessarily be harvested when 100% coverage is reached.

That which is claimed is:

1. A new and distinct variety of St. Augustine grass, substantially as herein illustrated and described, characterized by its distinctive combination of vegetative characteristics, its dark green foliage, its shade tolerance, cold and frost tolerance and drought tolernace.

* * * * *

UNITED STATES PATENT AND TRADEMARK OFFICE

CERTIFICATE OF CORRECTION

PATENT NO. : PP9395

DATED : December 5, 1995

INVENTOR(S) : Elmer R. Kirkland and Tobey A. Wagner

It is certified that error appears in the above-indentified patent and that said Letters Patent is hereby corrected as shown below:

Column 2, Fig. 10, Line 11, delete "shows DNA amplification profiles" and insert --compares node distances--.

Column 2, Line 28, delete "colr" and insert --color--.

Column 3, Line 59, delete "root" and insert --roots--.

Column 5, Line 41, delete "Raleight" and insert --Raleigh--.

Column 6, Line 67, delete "ESA" and insert --FSA--.

Column 7, delete Lines 4-6 and replace with --Callahan et al, *Golf Course Management*, page 80 (June 1993). Based on this study SS-100 and Floratam were determined to be genetically distinct--.

Column 8, Line 19, delete "it" and insert --is--.

Signed and Sealed this

Thirteenth Day of August, 1996

*Attest:*

Bruce Lehman

BRUCE LEHMAN

*Attesting Officer*

*Commissioner of Patents and Trademarks*